United States Patent [19]

Franck et al.

[11] Patent Number: 4,798,891

[45] Date of Patent: Jan. 17, 1989

[54] VINYLOGOUS PORPHYRINS

[75] Inventors: Burchard Franck; Martin Gosmann, both of Muenster, Fed. Rep. of Germany

[73] Assignee: BASF Aktiengesellschaft, Rheinland-Pfalz, Fed. Rep. of Germany

[21] Appl. No.: 108,706

[22] Filed: Oct. 15, 1987

[30] Foreign Application Priority Data

Oct. 22, 1986 [DE] Fed. Rep. of Germany ....... 3635820

[51] Int. Cl.$^4$ ........................................... C07D 487/22
[52] U.S. Cl. .................................. 540/472; 540/121; 540/145
[58] Field of Search ..................... 540/121, 145, 472

[56] References Cited

PUBLICATIONS

R. A. Berger and Eugene LeGoff; "The Synthesis of A 22π-Electron Tetrapyrrolic Macrocycle, [1,3,1,3,] Platyrin"; Pergamon Press Ltd. 1978; pp. 4225–4228 Tetrahedron Letters, No. 44.

E. LeGoff, and O. G. Weaver; "Synthesis of a [1,5,1,5,] Platyrin, a 26π-Electron Tetrapyrrolic Annulene"; J. Org. Chem. 1987, 52, 710–711.

*Primary Examiner*—Richard L. Raymond
*Attorney, Agent, or Firm*—Oblon, Fisher, Spivak, McClelland & Maier

[57] ABSTRACT

Compounds of the general formula I

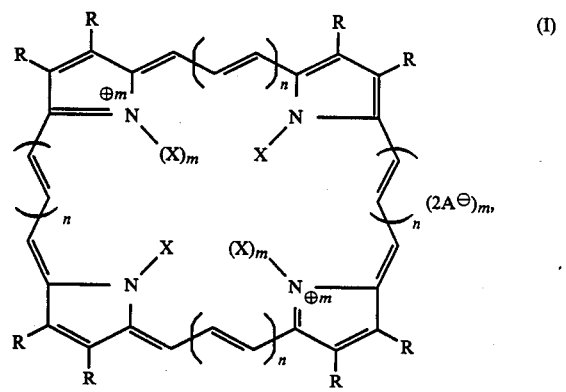

where the symbols n independently of one another are each 0, 1 or 2, m is 0 or 1, $A^\ominus$ is an anion, the radicals X independently of one another are each hydrogen, methyl or ethyl and the radicals R independently of one another are each hydrogen, unsubstituted or substituted alkyl, cycloalkyl or aryl, or two adjacent radicals R may furthermore be alkylene or, together with the carbon atoms to which they are bonded, may form an unsaturated or aromatic ring, with the proviso that one or more symbols n are not 0.

3 Claims, No Drawings

VINYLOGOUS PORPHYRINS

The present invention relates to compounds of the general formula I

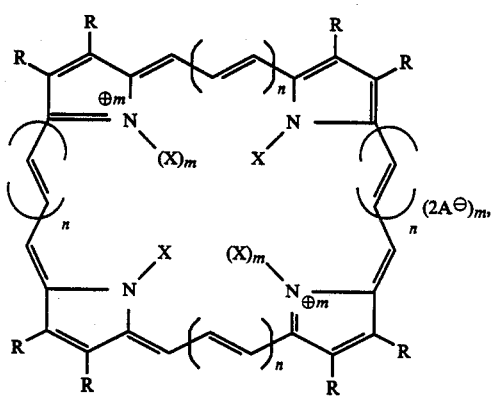

where the symbols n independently of one another are each 0, 1 or 2, m is 0 or 1, $A^{\ominus}$ is an anion, the radicals X independently of one another are each hydrogen, methyl or ethyl and the radicals R independently of one another are each hydrogen, unsubstituted or substituted alkyl, cycloalkyl or aryl, or two adjacent radicals R may furthermore be alkylene or, together with the carbon atoms to which they are bonded, may form an unsaturated or aromatic ring, with the proviso that one or more symbols n are not 0.

R is, for example, $C_1$–$C_{20}$-alkyl, which may be straight-chain or branched, $C_5$–$C_7$-cycloalkyl, $C_7$–$C_{10}$-phenylalkyl, $C_1$–$C_6$-alkyl which is substituted by $C_1$–$C_{12}$-alkoxycarbonyl, or phenyl which is unsubstituted or substituted by chlorine, bromine, cyano, $C_1$–$C_4$-alkyl or $C_1$–$C_4$-alkoxy.

Specific examples of radicals R are methyl, ethyl, propyl, butyl, hexyl, octyl, 2-ethylhexyl, decyl, dodecyl, octadecyl, hexadecyl, cyclohexyl, benzyl, 2-phenylethyl, phenyl, 3- and 4-chlorophenyl, 3- and 4-methylphenyl, 3- and 4-methoxyphenyl, 4-cyanophenyl, 4-bromophenyl, $C_1$–$C_{12}$-alkoxycarbonylmethyl or $C_1$–$C_{12}$ alkoxycarbonylethyl, where $C_1$–$C_{12}$-alkoxy may be, for example, methoxy, ethoxy, n-propoxy, isopropoxy, n-butoxy, isobutoxy, pentyloxy, hexyloxy, octyloxy, 2-ethylhexyloxy, decyloxy or dodecyloxy.

The compounds of the formula I can be prepared by converting a compound of the formula

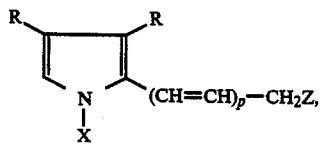

where Z is hydroxyl, alkoxy, acyloxy, chlorine, bromine or amino, p is 0, 1 or 2 and X and R have the stated meanings, in the presence of an acidic condensation agent, and then dehydrogenating the product. Where X is not hydrogen, the doubly charged cationic compounds are obtained.

Examples of anions $A^{\ominus}$ for this purpose are chloride, bromide, iodide, perchlorate, tetrachlorozincate, hexafluoroantimonate, hexachloroantimonate, hexafluorophosphate, sulfate, phosphate, acetate, trifluoroacetate, benzenesulfonate and tosylate.

Specific examples of radicals Z in addition to those stated above are $OCH_3$, $OC_2H_5$, $OC_3H_7$, $OC_4H_9$, $OCOCH_3$, $OCOC_2H_5$ and $OCOCH_2Cl$.

In the Examples, which describe the preparation, parts and percentages are by weight, unless stated otherwise.

The compounds of the formula I have very high extinctions and are useful, for example, as sensitizers for photochemical reactions or in optical information recording.

Of particular importance are compounds of the formula I in which the radicals R are each $C_1$–$C_4$-alkyl of $C_1$–$C_8$-alkoxycarbonylmethyl and n is 0 or 1. Among these compounds (I), particularly preferred ones are those in which n is 1 or two of the symbols n are each 1 and the other two symbols n are each 0.

EXAMPLE 1

Preparation of N,N',N'',N'''-tetramethyl-(26)-porphyrinogen

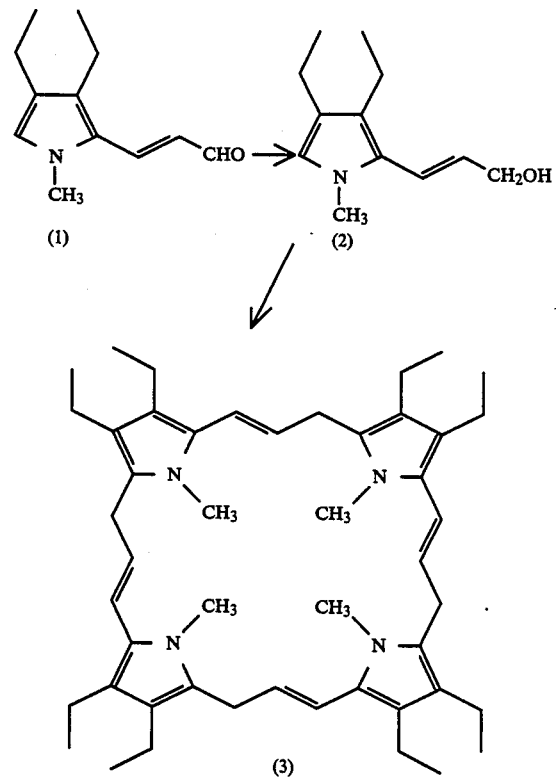

300 mg (1.47 millimoles) of N-methylpyrrylacrolein (1) were dissolved in 75 ml of absolute methanol under protective gas and were reduced to (2) with 300 mg (8 millimoles) of sodium borohydride in the course of 30 minutes. A solution of 40 mg of p-toluenesulfonic acid in 50 ml of analytical grade glacial acetic acid was then slowly added dropwise in the course of 1.5 hours. The mixture was stirred for a further 30 minutes and then partitioned between 100 ml of chloroform and 500 ml of water. Water was again added to the organic phase, and the pH was brought to 9. The solvent was distilled off, after which the product was subjected to preliminary purification by column chromatography (60 g of silica gel, chloroform). The crude product thus obtained was reprecipitated twice from a little methylene/chloride/methanol. It was filtered under suction through a microfrit and washed twice with a little cold 10:1 $CH_3OH/CH_2Cl_2$ and once with methanol. Drying under reduced pressure from an oil pump gave (3) as a colorless powder.

Yield: 69–83 mg (25–30%). Melting point 149°–250° C. (with decomposition)

$C_{48}H_{68}N$ (701.1) Calculated: C 82.23, H 9.78, N 7.99. Found: C 82.24, H 9.77, N 7.93.

$C_{48}H_{68}N$ Calculated 700.5444. Found 700.5434 (by mass spectrometry).

$^1$H-NMR (300 MHz, $CDCl_3$, ppm based on $CHCl_3$ with $\delta=7.27$); $\delta=1.08$ and 1.11 (2 t, J=7.5 Hz, 24H, $CH_2C\underline{H}_3$); 2.41 and 2.50 (2 q, J=7.5 Hz, 8H each, $C\underline{H}_2CH_3$); 3.28 (S, 12H, N—$CH_3$); 3.44 (d, J=5.5 Hz, 8H, CH=CHC$\underline{H}_2$); 5.6 (dt, J=16 and 5.5 Hz, 4H, CH=C$\underline{H}$CH$_2$); 5.97 (d, J=16 Hz, 4H, C$\underline{H}$=CHCH$_2$); MS (EI, 70 eV): m/z=700 (100%, M+); 685 (4%, M—$CH_3$); 671 (100%, M—$C_3H_5$); 525 (8%, ¾ M); 350 (56%, M/2); 335 (17%, 350-$CH_3$); 321 (22%, 350-$C_2H_5$); 176 and 174 (67%, 66%, monopyrrole units). IR (KBr, cm$^{-1}$): 2940, 29101 and 2855 (s, aliphatic. CH); 1630 (w, CH=CH); 1495 (m, aromat. C=C); 1445 (s, $\delta$-CH); 1372 (s, $\delta$-$CH_3$); 960 (s, trans R—CH=CH—R).

EXAMPLE 2

N,N',N'',N'''-tetramethyl-(3.3.3.3)-[26]porphyrin bistrifluoroacetate

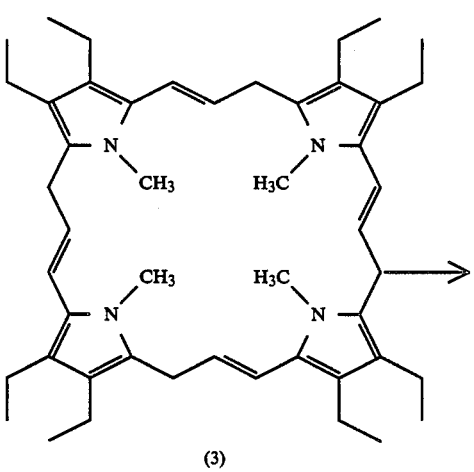

(3)

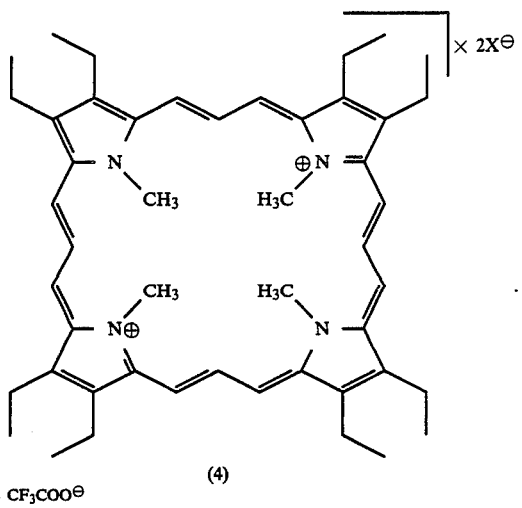

(4)

$X^\ominus = CF_3COO^\ominus$ 105.2 mg (0.15 millimole) of the N,N',N'',N'''-tetramethyl-[26]porphyrinogen (3) from Example 1 were stirred with 200 mg (0.60 millimole) of polymer base (diethylaminoethylpolystyrene, 3.0–3.2 milliequivalents of base/g of resin) in 150 ml of distilled chloroform under a protective gas, after which 12.85 ml (0.45 millimole) of a solution of bromine in carbon tetrachloride (560 mg of bromine/100 ml) was slowly added dropwise. The mixture was stirred overnight, the polymer base was filtered off and the solution was evaporated down in a rotary evaporator. The residue, which had a metallic green gloss, was purified twice by chromatography over silica gel (15 g; mobile phase 250:1 acetonitrile/trifluoroacetic acid). The combined product fractions from the second chromatography procedure were mixed with 50 ml of chloroform and then washed neutral with distilled water and stirred for a further 10 minutes with 100 mg of polymer base. The residue obtained after filtration and evaporation of the solvent gave, from methylene chloride/ether, the bistrifluoroacetate of [26]porphyrin (4) as an analytically pure, green powder, which was dried for 3 hours under reduced pressure from an oil pump. The product decomposed without melting.

Yield: 48.5 mg (35%).

Thin layer chromatography (silica gel; 250:1 $CH_3CN/CF_3COOH$) $R_f=0.20$ ($C_{48}H_{64}N_4^{2+}$) ($CF_3COO^-$)$_2$ (923.1). Calculated: C 67.66; H 6.99, N 6.07, F 12.35. Found: C 67.56, H 7.06, N 6.15, F 12.2 (Br 0.27).

UV/VIS (chloroform): $\lambda_{max}$ ($\Sigma$)=547 (909600) nm.

IR (KBr, cm$^{-1}$): 2955, 2920 and 2860 (m. aliphat. CH); 1675 (s, CO/trifluoroacetate).

$^1$H-NMR (300 MHz, $CDCl_3$): $\delta=-11.64$ (t, J=13.7 Hz, 4H, inner bridge H); −9.09 (s, 12H, N—$CH_3$); 2.43 (t, J=7.7 Hz, 24H, ethyl-$CH_3$); 4.99 (q, J=7.7 Hz, 16H, ethyl-$CH_2$); 13.67 (d, J=13.7 Hz, 8H, outer bridge H).

FD—MS ($CH_3CN$; 8 kV, 8–15 mA); m/z=697 (100%, $C_{48}H_{64}N_4$=M-2 $CF_3COO^-$); 695 (25%, M-2 $CF_3COOH$).

Solubility properties:

The compound dissolves in organic solvents, such as chloroform, methylene chloride, acetone, acetonitrile and methanol, but not in ether and nonpolar solvents.

EXAMPLE 3

Ethyl (1.3.1.3)-[22]porphyrin-octaacetate (7)

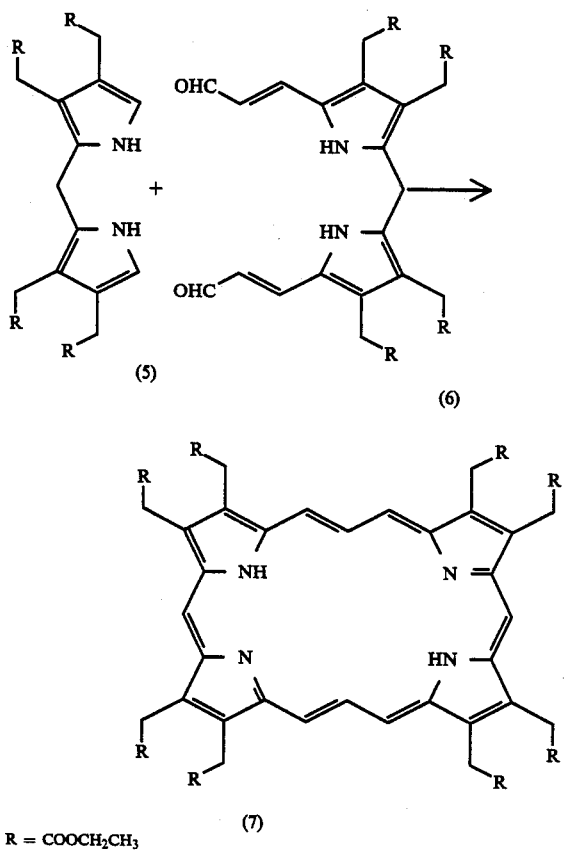

R = COOCH₂CH₃

24.5 mg (0.05 millimole) of dipyrrylmethane (5) and 29.9 mg (0.05 millimole) of dipyrryldiacrolein (6) in 150 ml of absolute methylene chloride were stirred for 20 minutes under argon before 1 ml of 33% strength hydrogen bromide in glacial acetic acid was slowly added. Stirring was continued for one hour at room temperature, after which 1.43 ml (0.05 millimole) of a solution of bromine in carbon tetrachloride (560 mg of bromine/100 ml) were added dropwise and the mixture was stirred for a further 2.5 hours. The green reaction mixture was washed neutral, first with 2N sodium bicarbonate solution and then with water, and was dried over sodium sulfate, and the solvent was separated off. The residue was purified by filtration over silica gel (5 g, 4:1 methylene chloride/ether) and reprecipitation from methylene chloride/ether. The product was a dark olive green solid which decomposed without melting.

Yield: 28 mg (53%) of porphyrin (7)

($C_{56}H_{66}N_4O_{16}$ (1051.2). Calculated: C 63.99; H 6.33, N 5.33. Found: C 64.15, H 6.36, N 5.26.

UV/VIS (chloroform): $\lambda_{max}$ ($\Sigma$)=485 (426000) nm, 505 (342500) nm, (chloroform/1% trifluoroacetic acid): $\lambda_{max}$ ($\Sigma$)=469 (1068000) nm.

IR (KBr, cm$^{-1}$): 2970, 2925 (w, aliphat. CH); 1723 (s; CO ester)

$^1$H-NMR (300 MHz, CDCl₃, ppm): $\delta$ = −8.19 (t, J=13.3 Hz, 2H, inner trimethine bridge H); 1.27 and 1.31 (2 t, J=7.1 Hz, 12H each, ester-CH₃); 4.32 (2 q, J=7.1 Hz, 8H each, ester-CH₂); 5.37 and 5.48 (2 s, 8H each, 22 porphyrin-CH₂); 10.59 (s, 2H monomethine bridge H); 11.91 (d, J=13.3 Hz, 4H, outer trimethine bridge H).

MS (EI; 70 eV; 3 kV acceleration voltage); m/z=1051+1 (16%), M+).

FD-MS (CHCl₃; 2 kV; 8-15 mA): m/z=1050±1 (100%, M+).

The compound dissolves in chloroform, methylene chloride and methanol.

We claim:

1. A compound of the formula I

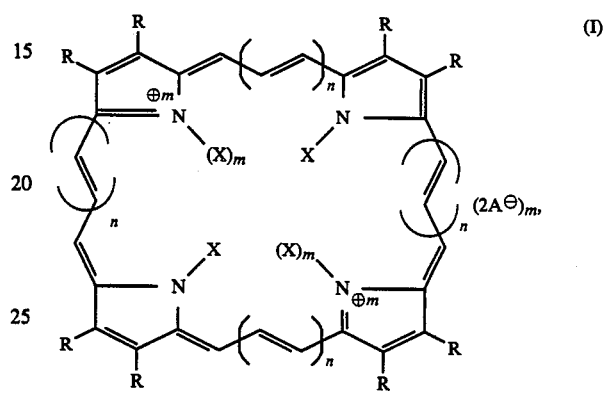

where the symbols n independently of one another are each 1 or 2, or two n's are each 1 and the other two are each 0, m is 0 or 1, A⁻ is an anion, the radicals X independently of one another are each hydrogen, methyl or ethyl and the radicals R independently of one another are each $C_1$-$C_{20}$-alkyl, $C_5$-$C_7$-cycloalkyl, $C_7$-$C_{10}$-phenylalkyl, $C_1$-$C_6$-alkyl substituted by $C_1$-$C_{12}$-alkoxycarbonyl, or phenyl or phenyl substituted by chlorine, bromine, cyano, $C_1$-$C_4$-alkyl or $C_1$-$C_4$-alkoxy, or two adjacent radicals R may furthermore be alkylene or, together with the carbon atoms to which they are bonded, may form an unsaturated or aromatic ring.

2. A compound of the formula I

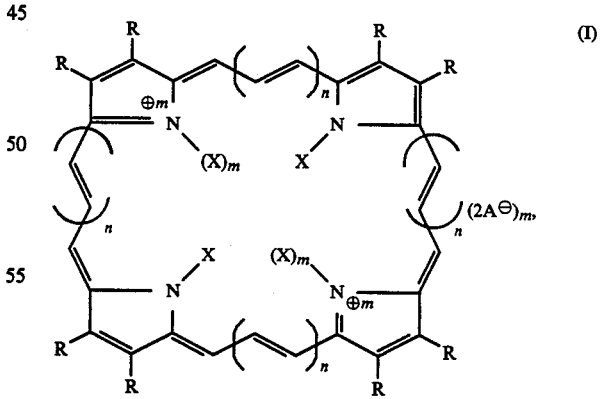

where m is 0 or 1, A⁻ is an anion, the radicals X independently of one another are each hydrogen, methyl or ethyl and the radicals R independently of one another are each $C_1$-$C_4$-alkyl or $C_1$-$C_8$-alkoxycarbonylmethyl and n is 1, or two n's are each 1 and the other two are each 0.

3. A compound of the formula I

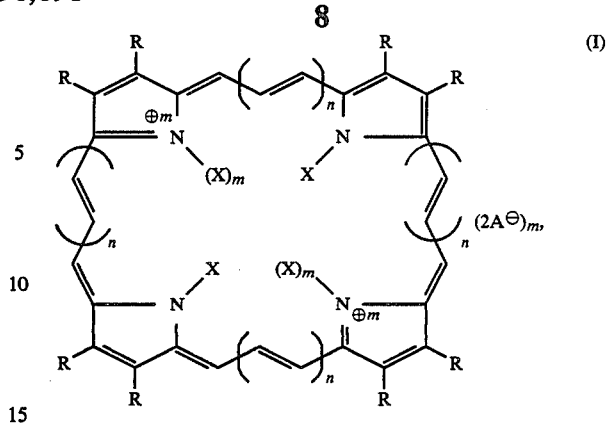

where the symbols n independently of one another are each 1 or 2, m is 0 or 1, $A^-$ is an anion, the radicals X independently of one another are each hydrogen, methyl or ethyl and the radicals R independently of one another are each $C_1$–$C_{20}$-alkyl, $C_5$–$C_7$-cycloalkyl, $C_7$–$C_{10}$-phenylalkyl, $C_1$–$C_6$-alkyl substituted by $C_1$–$C_{12}$-alkoxycarbonyl, or phenyl or phenyl substituted by chlorine, bromine, cyano, $C_1$–$C_4$-alkyl or $C_1$–$C_4$-alkoxy, or two adjacent radicals R may furthermore be alkylene or, together with the carbon atoms to which they are bonded may form an unsaturated or aromatic ring.

* * * * *